United States Patent
Rein et al.

(10) Patent No.: US 9,554,870 B2
(45) Date of Patent: Jan. 31, 2017

(54) DENTISTS' PREPARATION INSTRUMENT

(71) Applicant: Sirona Dental Systems GmbH, Bensheim (DE)

(72) Inventors: Matthias Rein, Lorsch (DE); Siegfried Goisser, Einhausen (DE); Metin Ertugrul, Rodermark (DE); Ralf Sutter, Weinheim (DE); Alexander Muhlbeyer, Neu Ulm (DE)

(73) Assignee: SIRONA DENTAL SYSTEMS GmbH, Bensheim (DE)

( * ) Notice: Subject to any disclaimer, the term of this patent is extended or adjusted under 35 U.S.C. 154(b) by 63 days.

(21) Appl. No.: 14/415,511

(22) PCT Filed: Jul. 17, 2013

(86) PCT No.: PCT/EP2013/065057
§ 371 (c)(1),
(2) Date: Jan. 16, 2015

(87) PCT Pub. No.: WO2014/012960
PCT Pub. Date: Jan. 23, 2014

(65) Prior Publication Data
US 2015/0164613 A1 Jun. 18, 2015

(30) Foreign Application Priority Data
Jul. 17, 2012 (DE) .................. 10 2012 212 480

(51) Int. Cl.
*A61C 1/05* (2006.01)
(52) U.S. Cl.
CPC ..................... *A61C 1/05* (2013.01)
(58) Field of Classification Search
CPC ........... A61C 1/05; A61C 1/052; A61C 1/055; A61C 1/057
(Continued)

(56) References Cited

U.S. PATENT DOCUMENTS 5,496,173 A 3/1996 Wohlgemuth
5,567,154 A 10/1996 Wohlgemuth
(Continued)

FOREIGN PATENT DOCUMENTS

DE 43 20 532 C1 9/1994
DE 44 28 039 C1 11/1995
(Continued)

OTHER PUBLICATIONS

International Preliminary Report on Patentability mailed Mar. 9, 2014 in PCT Application No. PCT/EP2013/065057.
(Continued)

*Primary Examiner* — Nicholas Lucchesi
(74) *Attorney, Agent, or Firm* — Fitzpatrick, Cella, Harper & Scinto

(57) ABSTRACT

A dentists' preparation instrument (1) comprises a turbine (4) for driving a tool (3) using compressed air, and a rotor (6) that is arranged in a turbine compartment (5), rotates about a longitudinal axis (7), and has blades (11) extending to a face (13) of the rotor (6). The turbine compartment (5) has a discharge port (12) for the compressed air towards a returning air duct (8). Said discharge port (12) is disposed in such a way that both the face (13) of the rotor (6) and parts of the blades (11) sweep past the discharge port (12) as the rotor rotates about the longitudinal axis (7). For deceleration purposes, the rotor (6) has a deceleration contour (9) on the face (13), said deceleration contour being formed by projections (14), and the turbine compartment (5) has a deceleration contour chamber (15) inside which the deceleration contour (9) is accommodated. The discharge port (12) in part also extends across the deceleration contour chamber (15).

27 Claims, 3 Drawing Sheets

(58) Field of Classification Search
USPC ............... 433/132; 415/904, 202, 198.1, 224
See application file for complete search history.

(56) References Cited

U.S. PATENT DOCUMENTS

| | | |
|---|---|---|
| 6,120,291 A | 9/2000 | Bareth et al. |
| 6,676,374 B2 | 1/2004 | Hashimoto et al. |
| 2007/0087308 A1* | 4/2007 | Flock .................... A61C 1/141 433/132 |
| 2011/0104636 A1* | 5/2011 | Takashi .................. A61C 1/05 433/132 |

FOREIGN PATENT DOCUMENTS

| | | |
|---|---|---|
| DE | 100 60 152 A1 | 6/2001 |
| EP | 0 497 139 A1 | 8/1992 |
| EP | 0 974 308 A1 | 1/2000 |

OTHER PUBLICATIONS

Office Action in German Patent Appln. No. 10 2012 212 480.2 mailed Feb. 19, 2013.
International Search Report mailed Oct. 30, 2013, in PCT Appln. No. PCT/EP2013/065057.

* cited by examiner

DENTISTS' PREPARATION INSTRUMENT

CROSS-REFERENCE TO RELATED APPLICATIONS

This application is a national stage entry of International Application No. PCT/EP2013/065057, filed Jul. 17, 2013, which claims priority to German Patent Appln. No. 10 2012 212 480.2 filed Jul. 17, 2012.

BACKGROUND OF THE INVENTION

Field of the Invention

The invention relates to a dentists' preparation instrument having a turbine for driving a tool by means of compressed air. A rotor disposed in a turbine compartment and rotating about a longitudinal axis has blades extending to a face of the rotor. The turbine compartment has a discharge port for the compressed air to a return air duct, wherein the discharge port is disposed in the turbine compartment in such a way that the face of the rotor passes by the discharge port laterally in rotation about the longitudinal axis.

Description of the Related Art

A dental turbine handpiece is known from EP 0 974 308 B1 with which, after the turbine has been shut down, because of the reduced pressure that develops due to after running in a turbine compartment upstream from the discharge port, a curtain flow is created for the purpose of preventing intake or reverse draw. This takes place due to the fact that a flow web protruding into the flow path deflects the flow from the discharge port inward. A flow groove may be placed upstream from the flow web disposed in the turbine compartment to make the flow step greater and to increase the efficiency. The compressed air flows out on one face of the blades and into an annular chamber provided in the turbine wheel, where it loses pressure. Both the annular chamber and parts of the blades lie opposite the discharge port. During functional operation, however, there is a break in the curtain flow because of the pressure gradient.

DE 100 60 152 B4 describes a dental turbine handpiece in which a rotor is equipped with a first and a second turbine wheel to increase the torque, and connecting ducts are provided to deflect the pressure medium from the first turbine wheel to the second turbine wheel. In one embodiment, the flow passes twice through the second turbine wheel, which decelerates the rotor and reduces the rotational speed.

The object of the invention is to achieve a reduction in the idling speed in order to improve the lifetime and noise behavior without restricting the effective power to an extent that would be of practical relevance.

BRIEF SUMMARY OF THE INVENTION

A dentists' preparation instrument having a turbine for driving a tool by means of compressed air according to the invention comprises a rotor disposed in a turbine compartment and rotating about a longitudinal axis, having blades that extend to a face of the rotor wherein the turbine compartment has a discharge port for the compressed air to a return air duct. The discharge port is disposed in the turbine compartment in such a way that the face of the rotor passes by the discharge port in rotation about the longitudinal axis and parts of the blades also pass by. The rotor has a disruptive contour formed by projections on the face and the turbine compartment has a disruptive contour space in which the disruptive contour is accommodated. The discharge port also extends partially beyond the disruptive contour space.

The disruptive contour on the turbine wheel in combination with a return air duct at the level of the disruptive contour creates a deceleration force that depends greatly on the rotational speed by utilizing the available airflow. A significant reduction in the rotational speed with only minor loss of torque is therefore achieved because the deceleration power in the third order is a function of the rotational speed, which means that only a low deceleration power is achieved at a low rotational speed and a disproportionately higher deceleration power is achieved at a higher rotational speed. Ribs or webs disposed on the face may be considered as projections in particular, an intermediate space being opened radically toward the discharge port between the projections.

To increase the deceleration effect, an eddy chamber which is connected to the discharge port may be provided in the return air duct, the width of this eddy chamber across the longitudinal axis and across the direction of flow of the return air duct amounting to at least 1.2 to 3 times a reference variable a, and its length LW in the direction of flow of the return air duct amounting to at least 0.3 to 1.5 times reference variable a, where the reference variable a is expressed either as a range from 0.5 to 1.5 times the smallest width w or as a range from 0.5 to 1.5 times the height HLA of the blades 11 of the rotor 6.

The function of the eddy chamber consists of creating turbulence in the exhaust air at the outlet to thereby intensify the interaction with the disruptive contour.

The turbine compartment may advantageously have a sharp discharge edge at the discharge port toward the eddy chamber. The intensification of the deceleration effect is achieved by the fact that discharge eddies are created at the discharge edge by the flow disruption, and are given space in the eddy chamber and also penetrate into the disruptive contour space, where they interact with the disruptive contour.

An advantageous refinement consists of the fact that the discharge port completely covers the disruptive contour in its height. This facilitates penetration of the return air into the disruptive contour space.

The discharge port may advantageously cover the blades over at least 70% of their height, preferably completely.

The face of the blades of the turbine may advantageously be covered by a disk, and the disruptive contour may protrude over the disk. This achieves a clear separation of function between the blades of the turbine and the disruptive contour, and only the disruptive contour space with the disruptive contour therein is acted upon by the exhaust air from the discharge port and/or from the eddy chamber. This has the advantage that, due to a clear separation of function, the design of the disruptive contours can be optimized with respect to the increase in flow resistance, whereas the blades can be designed optimally with regard to the increase in power. The disruptive contour can be designed so that it has a particularly high drag coefficient, also known as the cW value.

The disruptive contour may advantageously have a height of at least 5% of the height of the blades in the direction of the longitudinal axis, preferably approx. 20% and max. 50%.

An advantageous refinement may consist of the disruptive contour having ribs that are curved in the opposite direction with respect to the blades of the turbine. Therefore, the flow resistance in the disruptive contour is increased and thus the deceleration power is also increased.

For ease of production, it may be advantageous if the eddy chamber is free of additional guide devices.

The eddy chamber may advantageously extend over a range of max. 120°, but it is always disposed between the discharge port and the return air duct.

The eddy chamber may have rounded discharge edges in the return air duct to prevent flow losses at the typical operating rotational speeds.

BRIEF DESCRIPTION OF THE DRAWINGS

A device according to the invention is explained on the basis of the drawings, which show.

DETAILED DESCRIPTION OF THE INVENTION

Figure 1:
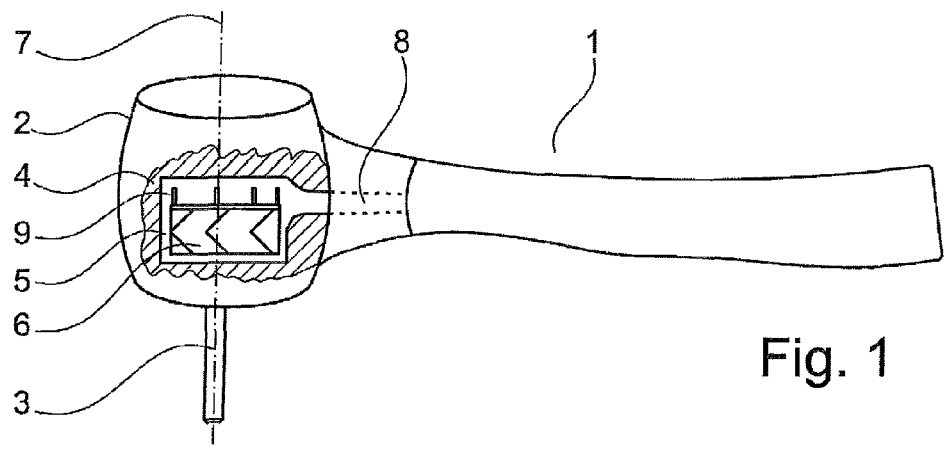
FIG. 1 a dentists' preparation instrument having a turbine for driving a tool by means of compressed air with a rotor having a disruptive contour in a side view.

FIG. 1 shows, schematically in a partially cutaway side view, a dentists' preparation instrument 1, having a turbine 4 that is acted upon by compressed air to drive a driven tool 3 that is mounted in a head part 2. The turbine 4 comprises a turbine compartment 5, in which a rotor 6 is mounted to rotate about a longitudinal axis 7. The bearing of the rotor 6 in the head part 2 itself and the cooperation of the rotor 6 with the tool 3 are not shown here; reference is made in this regard to the prior art, from which a wide variety of approaches are known from the documents cited in the introduction, for example.

In addition to a compressed air supply (not shown), a return air duct 8, which carries the compressed air out of the turbine compartment 5, is provided in the head part 2, so that compressed air is passed through a handle part to a coupling part of the preparation instrument, as is also known from the prior art.

FIG. 1 already shows that the rotor 6 is provided with a disruptive contour 9, which is disposed together with the rotor 6 in the turbine compartment 5. The functioning of this disruptive contour 9 and the interaction with the other functional modules are illustrated in FIGS. 2 and 3.

Figure 2:
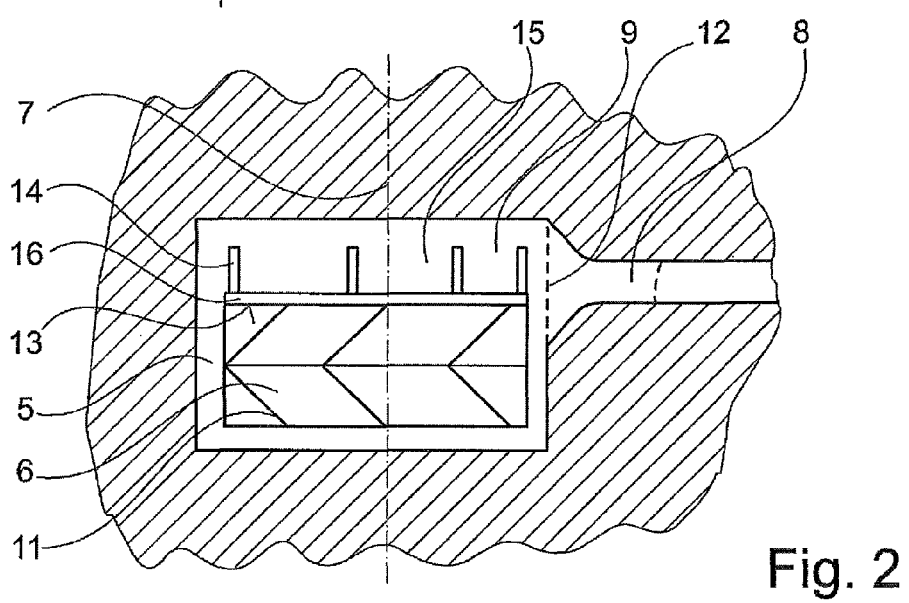
FIG. 2 the turbine compartment with the rotor having the disruptive contour from FIG. 1 in a side view in detail.
Figure 3:
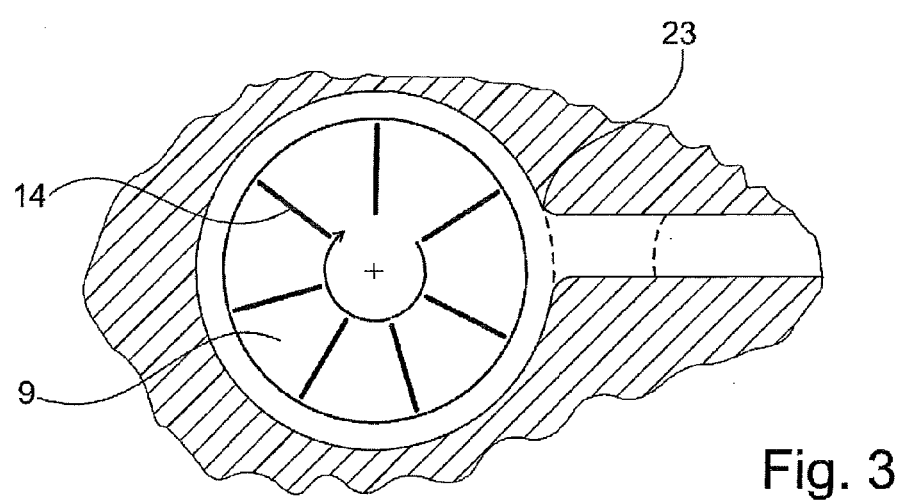
FIG. 3 the turbine compartment with the rotor having a disruptive contour from FIGS. 1 and 2 in a view of the disruptive contour in detail.

FIG. 2 shows the turbine compartment 5 with the rotor 6 in detail, this still being a basic diagram, just as before, in which the bearing of the rotor 6, for example, has been omitted for reasons of simplicity. The rotor 6 has blades 11, which deflect the compressed air provided for the drive of the turbine to improve efficiency. The compressed air flowing away from the blades 11, also referred to as exhaust air, leaves the turbine compartment 5 through a discharge port 12, which connects the turbine compartment 5 to the return air duct 8, and thus enters the return air duct 8.

The discharge port 12 is disposed in the turbine compartment 5 in such a way that both the face 13 of the rotor 6 and also parts of the blades 11 pass laterally by the discharge port 12 in rotation about the longitudinal axis 7.

The rotor 6 has the disruptive contour 9, which is formed by projections 14, on the face 13, so that, from the standpoint of function, a disruptive contour space 15, in which the disruptive contour is accommodated, is formed within the turbine compartment 5. It is important that the discharge port 12 also extends partially over the disruptive contour space 15.

As a result, the discharge port 12 has a discharge cross section of such dimensions that a portion of the blades 11 as well as at least a portion of the disruptive contour 9 pass by the discharge port.

The cross section of the discharge port 12 may correspond to the cross section of the return air duct 8, but there may also be a reduction in cross section from the cross section of the discharge port 12 to the cross section of the return air duct 8.

Fundamentally, it should first be pointed out that the exhaust air flowing around the axis of the rotor changes directions in the transition to the discharge duct. The speed of the exhaust air, which is initially directed tangentially, develops progressively a velocity component directed radially to the rotor axis immediately before entering the discharge duct. The velocity component directed in the circumferential direction of the exhaust air decreases by comparison. Therefore, a relative velocity is established between the exhaust air and the rotor. This velocity difference creates an area acted upon by pressure on the downstream-facing side of the disruptive contour. The deceleration pressure created in this way depends on the rotational speed in the second order.

The face 13 of the blades is covered by a disk 16 and the disruptive contour 9 protrudes beyond the disk 16. The flow path is such that the compressed air deflected by the blades flows into the discharge port 12, where some of it also enters the disruptive contour space 15, from which it can then escape again through the same discharge port 12 if allowed by the pressure difference. Other clearance losses also result in compressed air penetrating into the disruptive contour space. On the whole, however, it is true that the disruptive contour is exposed to only a substream of the compressed air.

The projections 14 on the disruptive contour 9 may also be formed by ribs or webs protruding beyond the face, as shown by the view of the disruptive contour in FIG. 3. The projections are disposed on the outside circumference, where an intermediate space between the projections is open radially toward the discharge port.

Figure 3A:
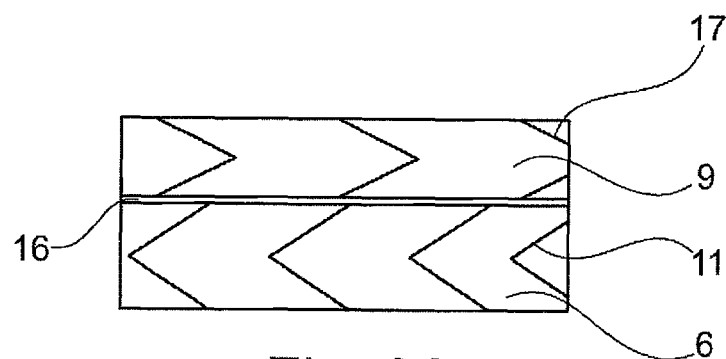
FIG. 3A a rotor having an opposite disruptive contour in a side view.
Figure 3B:
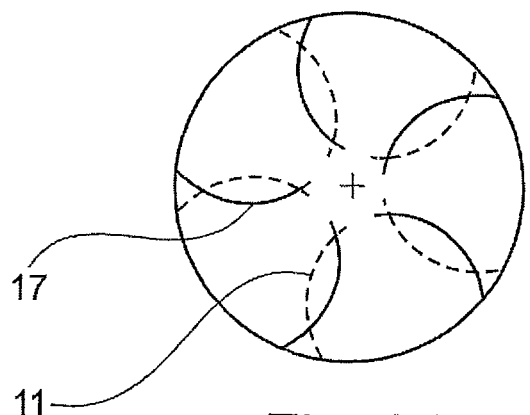
FIG. 3B the rotor from FIG. 3A in a view from above.

The projections 14 of the disruptive contour may also be embodied in the form of ribs 17, which are curved in the opposite direction from the blades 11 of the rotor to increase the cW value, shown schematically in FIGS. 3A and 3B. Here again, the face 13 of the blades 11 of the rotor 6 is covered with a disk 16.

The number of projections, when they are embodied in the form of webs or ribs extending radially or with a radial curvature away from the longitudinal axis, may correspond to the number of blades, the rotor having seven blades in many cases, all of them disposed in a uniform distribution over the circumference. Preferably, however, at least two and at most twice as many as the number of blades are provided.

Figure 4:
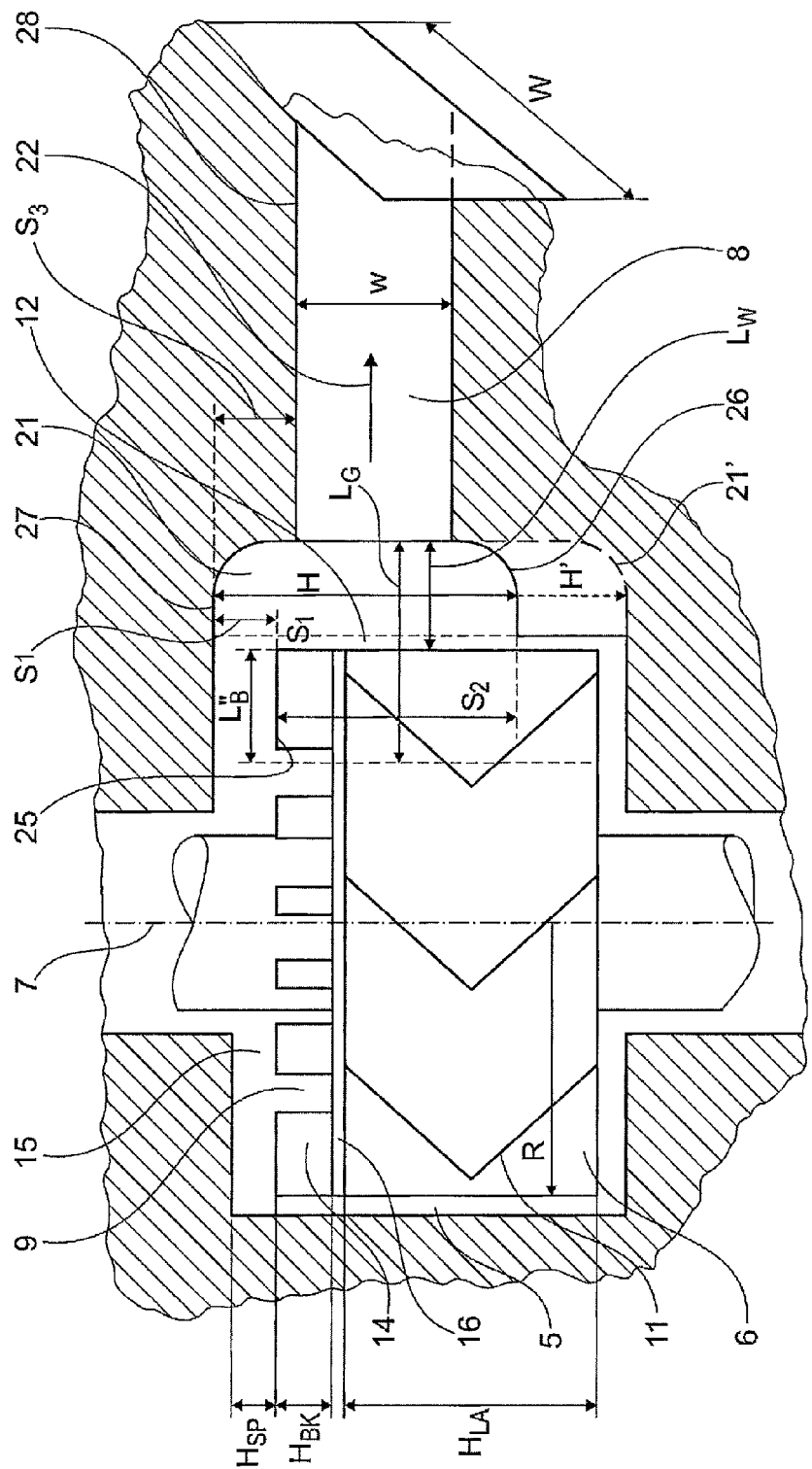
FIG. 4 an embodiment of the turbine compartment with the rotor having a disruptive contour from FIG. 2, with an additional eddy chamber in a side view in detail.

FIG. 4 shows in a side view one embodiment of the turbine compartment 5 with the rotor 6 having the disruptive contour 9 disposed on the disk 16 from FIG. 2 with an eddy chamber 21 disposed between the turbine compartment 5 and the return air duct 8. The discharge port 12 of the turbine compartment 5 develops into the eddy chamber 21, the height H of which in the direction of the longitudinal axis 7, as shown, can cover only a portion of the blades 11 but may also go over the total height of the turbine compartment 5, represented as a dotted line 21' and having the height H'.

The interaction with the disruptive contour 9 is intensified because the relative velocity between the exhaust air and the rotor 6 becomes greater the greater the velocity difference between the velocity vectors of the exhaust air and of the rotor 6 at the discharge port 12 upstream from the return air duct 8. This difference can be intensified by the fact that turbulence is created in the exhaust air directly at the discharge port 12 and upstream from the return air duct 8, so that portions of the exhaust air may even flow in the opposite direction from the direction of rotation of the rotor, which is not shown here.

The eddy chamber 21, which is disposed upstream from the return air duct 8 in the direction of flow in the head housing, has a length LW in the direction of flow of the return air duct 8, indicated by the arrow 22. The length LB is defined by the radial extent of the disruptive contour, projected onto a plane running through the longitudinal axis 7 and the projections 14 on the disruptive contour 9 itself and should correspond at least to the radial extent of the disruptive contour on the rotor which cooperates definitively with an eddy developing in the eddy chamber 21. This eddy is not shown for reasons of simplicity. The total length LG having a deceleration effect available to the eddy is given by the length LW of the eddy chamber and the length LB of the disruptive contour.

Figure 5:
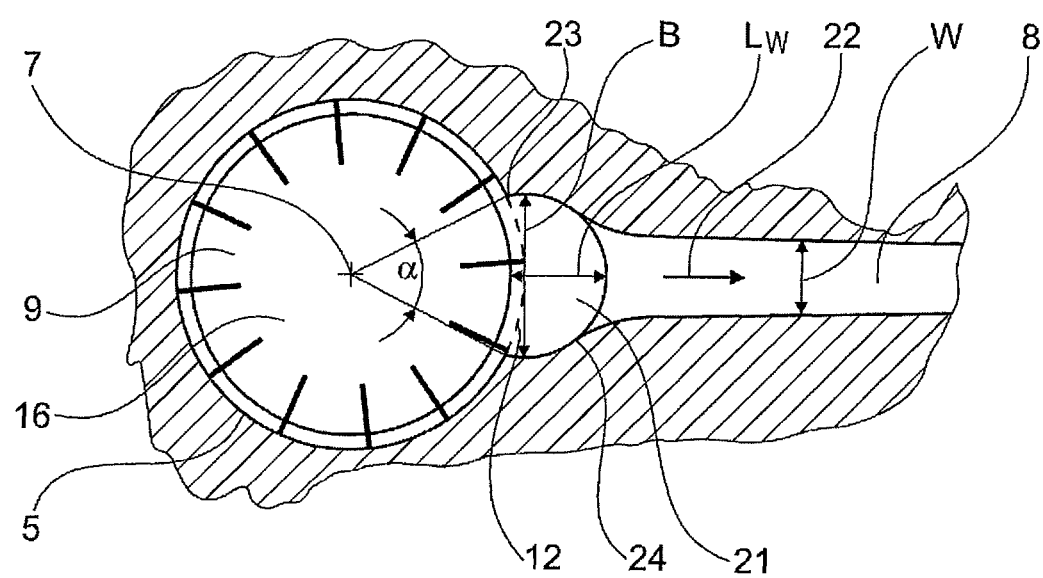
FIG. 5 the embodiment according to FIG. 4, where the rotor has the disruptive contour from FIG. 3 in a view of the disruptive contour in detail.

FIG. 5 shows the eddy chamber 21 in a view of the disruptive contour 9, which is disposed on the disk 16. It can be seen here that the eddy chamber 21 is connected to the discharge port 12 of the turbine compartment 5 and has a width B across the longitudinal axis 7 and across the direction of flow of the return air duct 8, represented by the arrow 22.

The eddy chamber 21 itself has rounded discharge edges 24 at its transition to the return air duct 8 in order to reduce the flow resistances in the return air duct itself.

One possible extent of the eddy chamber 21 is described as follows with reference to FIGS. 4 and 5, wherein both the smallest width w of the return air duct 8 or a measure HLA based on the height of the blades 11 of the rotor 6, approximately at least half the height HLA and max. the double height HLA, can be selected as the reference variable a. The smallest width w is understood to be the greatest measure a sphere may have in order to pass through the cross section. In the case of a circular hole, this is the diameter of the hole, or in the case of a cube, it is the short side of the cross section. There may also be a largest width W, which is shown schematically for a rectangular cross section of the return air duct 8.

Thus, the reference variable a may be expressed either as a range from 0.5 to 1.5 times the smallest width w or as a range from 0.5 to 1.5 times the height HLA of the blades 11 of the rotor 6.

A range of $0.5*a<H<2*a$, preferably $H=a$ or $H=HBK+HLA$, has proven especially suitable for the height H of the eddy chamber 21. The length LW of the eddy chamber 21 is in a range of $0.3*a<LW<1.5*a$, preferably $LW=a$. The width B of the eddy chamber 21 is in a range $1.2*a<B<3*a$, preferably $B=1.2*a$. The length ratio of the length LB of the disruptive contour to the length LW of the eddy chamber 21 is preferably 1/2, so that a ratio of the length LB of the disruptive contour to the total length LG of 1/3 is obtained for a total length LG.

The range of $0.05*HLA<HBK<0.5*HLA$ has proven to be especially suitable as the height HBK of the disruptive contour, again based on the height HLA of the blades 11 of the rotor 6, preferably $HBK=0.2*HLA$.

The length LB of the disruptive contour 9 is defined by the radial extent of the disruptive contour 9 projected onto a plane, which runs through the longitudinal axis 7 and the projections 14 of the disruptive contour 9 itself and lies in a range of $0.1*R<LBK<0.7*R$, preferably $LBK=0.3*R$, based on the radius R of the rotor 6.

The width BBK of the disruptive contour 9, i.e., the extent of a projection 14 in the circumferential direction, lies in a range of $0.05$ mm$<BBK<3.0$ mm, preferably $BBK=0.1$ mm.

The disruptive contour 9 corresponds in diameter to the rotor 6 but may also be reduced if required by the spatial conditions and the fine tuning of the deceleration power by means of the lever arm and the deceleration surface.

The position of the eddy chamber 21 relative to the disruptive contour 9 is also important. To illustrate this, FIG. 4 shows that the projections 14 of the disruptive contour 9 have a top edge 25 facing away from the blades 11.

The eddy chamber 21 is defined in the axial direction of the rotor 6 by the bordering surfaces 26 and 27. The distance S1, also given as the height HSP, between the top edge 25 of the disruptive contour 9 and the top bordering surface 27 of the eddy chamber 21 is at least 0.1 mm and max. 10 times the height HBK of the disruptive contour, preferably 2×HBK. The distance S2 between the top edge 25 and the lower bordering surface 26 is at least $0.5*a$ and max. $3*a$, ideally $1.5*a$.

In addition, the position of the eddy chamber 21 relative to the return air duct 8 is relevant. The distance s3 between the upper bordering surface 27 and the top side 28 of the return air duct 8 may be at least zero and max. $s3<(s1+HBK+HLA)$ and $s3=s1+HBK$ is particularly suitable.

The eddy chamber 21 itself is free of additional guide devices and extends in the direction of rotation of the rotor 6 over an angle range alpha in the present case of approx. alpha equal to 45°, represented in FIG. 5.

It is true of all embodiments that the turbine compartment may have a sharp discharge edge 23 at the discharge port 12 to the return air duct 8 or to the eddy chamber 21, as shown in FIGS. 3 and 5, so that there is a strong discharge eddy that cooperates with the disruptive contour 9.

It has been found that the flow conditions at the discharge port cooperate with the disruptive contour in such a way that a deceleration is induced at higher rotational speeds, whereas there is only an insignificant loss of torque at lower rotational speeds.

For an understanding of the invention it is pointed out that other fluids may also be used instead of compressed air. In addition, compressed air is also mentioned in general when a partial depressurization has taken place and the pressure difference from atmospheric pressure is only minor, as is the case with the exhaust air in the return air duct 8, for example.

The invention claimed is:
1. A dental apparatus, comprising:
 a turbine compartment that includes a discharge port;
 a turbine constructed to drive a tool by compressed air,
  wherein the turbine includes a rotor located within the turbine compartment that is constructed to rotate about a longitudinal axis of the rotor, wherein the turbine includes:

(i) a plurality of blades that extend up to a face of the rotor, and
(ii) a disruptive contour located in a disruptive contour space and formed by projections that protrude beyond the face of the rotor; and an eddy chamber connected to the discharge port and a return air duct, wherein the eddy chamber is constructed to create turbulence in exhaust air from the turbine compartment, wherein the disruptive contour includes an intermediate space between the projections that is open radially toward the discharge port, and wherein the discharge port, the face of the rotor, and the plurality of blades are arranged such that both the face of the rotor and parts of the plurality of blades pass by the discharge port during a rotation about the longitudinal axis.

2. The dental apparatus according to claim 1, wherein a width of the eddy chamber across the longitudinal axis and across a direction of flow of the return air duct is 1.2 to 3 times a reference variable,
wherein a width of the eddy chamber in the direction of flow of the return air duct is 0.3 to 1.5 times the reference variable, and
wherein the reference variable is either (i) a range from 0.5 to 1.5 times a smallest width of the return air duct, or (ii) a range from 0.5 to 1.5 times a height of the plurality of blades.

3. The dental apparatus according to claim 1, wherein the turbine compartment has a sharp discharge edge at an intersection of the discharge port and the eddy chamber.

4. The dental apparatus according to claim 1, wherein the discharge port covers the disruptive contour in height.

5. The dental apparatus according to claim 1, wherein the discharge port covers the plurality of blades in height.

6. The dental apparatus according to claim 1, wherein a face of the plurality of blades of the turbine is covered by a disk and the disruptive contour protrudes beyond the disk.

7. The dental apparatus according to claim 1, wherein a height of the disruptive contour in the direction of the longitudinal axis is between 5% and 50% of a height of the plurality of blades.

8. The dental apparatus according to claim 7, wherein the height of the disruptive contour in the direction of the longitudinal axis is 20% of the height of the plurality of blades.

9. The dental apparatus according to claim 1, wherein the projections are ribs that are curved in an opposite direction from the plurality of blades.

10. The dental apparatus according to claim 1, wherein the eddy chamber does not include guide devices.

11. The dental apparatus according to claim 1, wherein the eddy chamber extends over an angular range, in a direction of rotation about the longitudinal axis of the rotor, of up to 120°.

12. The dental apparatus according to claim 1, wherein the eddy chamber has rounded discharge edges.

13. The dental apparatus according to claim 1, wherein the projections are ribs or webs.

14. A dental apparatus, comprising:
a turbine compartment that includes a discharge port;
a turbine constructed to drive a tool by compressed air, wherein at least a portion of the turbine is located within the turbine compartment, and wherein the turbine includes:
a rotor,
a plurality of blades that extend up to a face of the rotor, and
a disruptive contour in the form of a projection that protrudes beyond the face of the rotor; and
an eddy chamber connected to the discharge port and a return air duct, wherein the eddy chamber is constructed to create turbulence in exhaust air from the turbine compartment.

15. The dental apparatus according to claim 14, wherein the disruptive contour includes a plurality of projections and an intermediate space between the plurality of projections that is open radially toward the discharge port, and
wherein the discharge port, the face of the rotor, and the plurality of blades are arranged such that both the face of the rotor and parts of the plurality of blades pass by the discharge port during a rotation about a longitudinal axis of the rotor.

16. The dental apparatus according to claim 14, wherein a width of the eddy chamber across a longitudinal axis of the rotor and across a direction of flow of the return air duct is 1.2 to 3 times a reference variable,
wherein a width of the eddy chamber in the direction of flow of the return air duct is 0.3 to 1.5 times the reference variable, and
wherein the reference variable is either (i) a range from 0.5 to 1.5 times a smallest width of the return air duct, or (ii) a range from 0.5 to 1.5 times a height of the plurality of blades.

17. The dental apparatus according to claim 14, wherein the turbine compartment has a sharp discharge edge at an intersection of the discharge port and the eddy chamber.

18. The dental apparatus according to claim 14, wherein the discharge port covers the disruptive contour in height.

19. The dental apparatus according to claim 14, wherein the discharge port covers the plurality of blades in height.

20. The dental apparatus according to claim 14, wherein a face of the plurality of blades of the turbine is covered by a disk and the disruptive contour protrudes beyond the disk.

21. The dental apparatus according to claim 14, wherein a height of the disruptive contour in a direction of a longitudinal axis of the rotor is between 5% and 50% of a height of the plurality of blades.

22. The dental apparatus according to claim 21, wherein the height of the disruptive contour in the direction of the longitudinal axis is 20% of the height of the plurality of blades.

23. The dental apparatus according to claim 14, wherein the projection is a rib that is curved in an opposite direction from the plurality of blades.

24. The dental apparatus according to claim 14, wherein the eddy chamber does not include guide devices.

25. The dental apparatus according to claim 14, wherein the eddy chamber extends over an angular range, in a direction of rotation about a longitudinal axis of the rotor, of up to 120°.

26. The dental apparatus according to claim 14, wherein the eddy chamber has rounded discharge edges.

27. The dental apparatus according to claim 14, wherein the projection is a rib or web.

* * * * *